United States Patent [19]

Patterson et al.

[11] Patent Number: 6,110,905
[45] Date of Patent: Aug. 29, 2000

[54] LONG-ACTING OXYTETRACYCLINE COMPOSITION

[75] Inventors: Alan Patterson, Belfast; Drew Holmes, Bryansford, both of United Kingdom

[73] Assignee: Norbrook Laboratories Limited, Newry, United Kingdom

[21] Appl. No.: 09/159,680

[22] Filed: Sep. 24, 1998

Related U.S. Application Data

[63] Continuation of application No. 08/765,475, Apr. 8, 1997, abandoned.

[51] Int. Cl.$^7$ .................................................... A61K 31/65
[52] U.S. Cl. ........................................... 514/152; 514/153
[58] Field of Search ...................................... 514/152, 153

[56] References Cited

U.S. PATENT DOCUMENTS

| | | |
|---|---|---|
| 4,772,460 | 9/1988 | Malook et al. .......................... 514/152 |
| 5,075,295 | 12/1991 | Zupan et al. ............................ 514/152 |

FOREIGN PATENT DOCUMENTS

| | | |
|---|---|---|
| 0 038 013 | 10/1981 | European Pat. Off. ................ 514/152 |
| 0 096 942 | 12/1983 | European Pat. Off. . |
| 2 081 434 | 12/1971 | France . |
| 20 11 793 | 9/1970 | Germany . |

*Primary Examiner*—Jerome D. Goldberg
*Attorney, Agent, or Firm*—Venable; John P. Shannon

[57] ABSTRACT

An injectable composition of higher residual effect with reduced detrimental effects such as pain at injection site, swelling, tissue irritancy or necrosis and containing as active principle a tetracycline compound, either as the free base or a salt thereof with a physiologically acceptable acid, complexed with a substantially equimolar amount of a magnesium compound, is solubilized in a water miscible solvent system comprising, either (i) a) glycerol formal in an amount of from about 10 to 50% v/v; with b) polyethylene glycol in an amount of from about 1 to 15% v/v; or (ii) from about 25 to about 75% v/v of N-methylpyrrolidone, the composition optionally containing a pH modifier in an amount sufficient to maintain a physiochemically acceptable pH, the balance being made up with water q.s.

19 Claims, No Drawings

LONG-ACTING OXYTETRACYCLINE COMPOSITION

This application is a continuation of application Ser. No. 08/765,475 of Alan Patterson et al., filed Apr. 8, 1997, entitled "LONG-ACTING OXYTETRACYCLINE COMPOSITION", now abandoned.

This invention relates to injectable formulations containing tetracyclines, particularly oxytetracycline, which exhibit higher residual effect with less of the known detrimental effects such as pain at injection site, swelling, tissue irritancy or necrosis.

Preparation of pharmaceutical compositions containing tetracyclines and oxytetracycline in particular has always presented a challenge due to aqueous solubility constraints which firstly have impact upon composition stability, and secondly upon parenteral administration.

Prior art oxytetracycline compositions have exhibited relatively high viscosity at low temperatures which makes injection difficult, have shown poor stability and suffered limitations on strength of active principle. Thus considerable research has gone into determining suitable complexing agents and more favourable co-solvents to address these shortcomings. A review of the art suggests that presence of calcium, and especially magnesium in the formulation now appears mandatory as a complexing agent and whereas some improvements have been made in stability and delivery by adopting various co-solvent systems, higher concentration loadings and residual effect remain areas in which improvements are needed. This is especially of interest for veterinary purposes where the need is to deliver high effective doses with minimum effort in animal handling and detrimental effect on the animal requiring treatment.

At the current time prior art so-called "long-acting" oxytetracycline formulations typically contain 200 mg/ml oxytetracycline and are administered at 20 mg/kg body weight, having activity as determined by residual blood levels of oxytetracycline detectable for up to about four days or so.

An object of this invention is to provide a composition of substantially greater long acting effect whilst minimising to the greatest extent possible the defects observed in previously proposed formulations. In particular the invention to be particularly described hereinbelow provides for administration of an oxtetracycline formulation at dose rates of from 10 to 40 mg/kilogram bodyweight, giving at 30 mg/kg in animals an extended duration of effective plasma levels against susceptible organisms in excess of 9 days which is a surprising achievement in the light of the known prior art.

Solubility of oxytetracycline in non-aqueous solvents was considered by Eugene Gans and Takeru Higuchi, Journal of the American Pharmaceutical Association, 1957, Vol XLVI, pp 587–591.

The patent literature in this area is extensive and one could refer to the following patents which are illustrative of the decades of research carried out on formulation of tetracycline compositions: GB-A-894 619, GB-A-1 131 007, GB-A-1 250 304, GB-A-1 286 351, GB-A-1 427 882, GB-A-1 494 558, GB-A-1 508 601, GB-A-1 514 838, GB-A-1 520 197, GB-A-1 538 903 GB-A-1 563 478, GB-A-1 592 053, GB-B-2 047 097; EP-B-38 103, EP-B-96 942; U.S. Pat. No. 2,516,080, U.S. Pat. No. 2,980,584, U.S. Pat. No. 2,990,331, U.S. Pat. No. 3,062,717, U.S. Pat. No. 3,219,529, U.S. Pat. No. 3,557,280, U.S. Pat. No. 3,712,949, U.S. Pat. No. 3,957,972, U.S. Pat. No. 4,011,313, U.S. Pat. No. 4,018,889, U.S. Pat. No. 4,020,162, U.S. Pat. No. 4,126,680, U.S. Pat. No. 4,386,083, U.S. Pat. No. 4,399,127, U.S. Pat. No. 4,772,460, U.S. Pat. No. 4,957,972, and U.S. Pat. No. 5,075,295.

From these documents it is apparent that a variety of water-dispersible complex-stabilisers or water-miscible co-solvents have been proposed including 2-pyrrolidone, polyvinyl pyrrolidone, polyethylene glycols, caprolactam, 2-piperidone, and glycerol formal (a reaction product of glycerol and formaldehyde) in specific formulations. However it is by no means clear that the said co-solvents are equally interchangeable nor can the effect of such a change be entirely predictable for a given formulation.

U.S. Pat. No. 4,386,083 proposes use of glycerol formal in conjunction with magnesium acetate and magnesium chloride, whilst U.S. Pat. No. 4,772,460 proposes use of N-methylpyrrolidone (1-methyl-2-pyrrolidone) and a soluble magnesium compound. U.S. Pat. No. 5,075,295 is particularly directed to a composition aiming to achieve up to 30% oxytetracycline, which contains polyethylene glycol 400 and magnesium oxide, but examples given only appear to show a capability of achieving up to 25% oxytetracycline and there is to applicant's knowledge no current commercially available product capable of achieving greater than 20%.

Accordingly this invention provides a composition containing as active principle a tetracycline compound, either as the free base or a salt thereof with a physiologically acceptable acid, complexed with a substantially equimolar amount of a magnesium compound, solubilised in a water miscible solvent system comprising, either (i) a) glycerol formal in an amount of from about 10 to about 50% v/v; with b) polyethylene glycol in an amount of from about 1 to 15% v/v; or (ii) from about 25 to about 75% v/v of N-methylpyrrolidone, said composition optionally containing a pH modifier in an amount sufficient to maintain a physiochemically acceptable pH, the balance being made up with water q.s.

The composition optionally contains a thickener such as polyvinyl pyrrolidone in an amount of up to 10% w/v, and may contain usual formulation aids or auxiliaries typically used for such formulations. Thus the composition may contain antioxidants, e.g. sodium formaldehyde sulphoxylate and pH adjusting agents e.g. monoethanolamine, to provide a preferred pH range of from about 7.5 to about 9.5, more preferably from about 8.5 to about 9.0.

Preferably the composition contains a magnesium compound such as magnesium oxide or a salt e.g magnesium chloride.

The preferred compositions contain oxytetracycline as the base or its hydrochloride in an amount of from about 15 to about 35% w/v, complexed with an equimolar ratio of a magnesium compound, preferably a salt, solubilised in a solvent system comprising polyethylene glycol in an amount of from about 1 to about 15% v/v and glycerol formal in an amount of from about 10 to about 50% v/v. In particular the most preferred composition contains about 30% w/v oxytetra-cycline, about 40% glycerol formal, about 10% v/v poly-ethylene glycol with a magnesium-containing complexing agent or stabiliser, antioxidant and water making up the balance. In that composition magnesium oxide is suitably present in an amount of about 2.7% w/v and, as antioxidant, sodium formaldehyde sulphoxylate in an amount of about 0.4% w/v may be used. Thus according to the present invention there is provided a formulation capable of providing from about 10 to about 40 mg/kg bodyweight consisting of:

| Oxytetracycline | 300 mg |
|---|---|
| Magnesium oxide | 27 mg |
| Sodium formaldehyde sulphoxylate | 4 mg |
| Glycerol formal | 0.4 ml |
| Polyethylene glycol | 0.1 ml |
| Monoethanolamine | q.s. pH 8.6 to 8.8 |
| Water for injections | to 1 ml |

The invention will now be further described by way of example for the purposes of practical illustration only.

An oxytetracycline formulation was prepared according to the procedure indicated below using the following components:

A controlled environment having an inert atmosphere was provided within which suitable mixing and temperature controllable heating apparatus was assembled. A nitrogen blanket is considered suitable for this purpose. The above components of the proposed composition were mixed by initially mixing a proportion of the total water with the selected solvents. The sodium formaldehyde sulphoxylate, magnesium oxide and oxytetra-cycline were added sequentially whilst mixing continuously and maintaining a temperature of approximately 65° C. until all the constituents have dissolved. Thereafter, the composition is cooled to below 30° C. and the pH is adjusted to lie within the range of 8.0 to 9.0, in this case by adding a sufficient amount of mono-ethanolamine. Finally the volume is made up with water, the pH checked and adjusted if necessary, and the composition is filtered through a 0.2 $\mu$m filter and filled into appropriate containers.

In alternative embodiments, where use of a thickener such as polyvinyl pyrrolidone is called for then it should preferably be added after the sodium formaldehyde sulphoxylate.

The following Tables provide details of Examples 1 to 14 each of which provided compositions showing excellent stability and which achieved the desired dosage levels and long acting effect.

TABLE 1

| INGREDIENTS | EXAMPLE | | | | | | | | | |
|---|---|---|---|---|---|---|---|---|---|---|
| | 1 | 2 | 3 | 4 | 5 | 6 | 7 | 8 | 9 | 10 |
| Oxytetracycline (% w/v) | 30.0 | 30.0 | 30.0 | 30.0 | 30.0 | 30.0 | 30.0 | 30.0 | 15.0 | 35.0 |
| Magnesium Oxide (% w/v) | 2.7 | 2.7 | 2.7 | 2.7 | 2.7 | 2.7 | 2.7 | 13.25* | 1.3 | 3.06 |
| Sodium Formaldehyde Sulphoxylate (% w/v) | 0.4 | 0.4 | 0.4 | 0.4 | 0.4 | 0.4 | 0.4 | 0.5 | 0.4 | 0.4 |
| Glycerol Formal (% v/v) | 30.0 | 30.0 | 30.0 | 35.0 | 35.0 | 35.0 | 40.0 | 40.0 | 40.0 | 40.0 |
| Polyethylene Glycol 200 (% v/v) | 10.0 | 15.0 | 20.0 | 10.0 | 15.0 | 20.0 | 10.0 | 10 | 10.0 | 10.0 |
| Polyvinyl Pyrrolidone K12 (% w/v) | | | 3.0 | | | | | | | |
| Water to (% v/v) | 100 | 100 | 100 | 100 | 100 | 100 | 100 | 100 | 100 | 100 |

*Magnesium Chloride

| Active Ingredient - | |
|---|---|
| Oxytetracycline | 30% w/v |
| Excipients - | |
| Magnesium oxide | 2.7% w/v |
| Sodium formaldehyde sulphoxylate | 0.4% w/v |
| Glycerol formal | 40% w/v |
| Polyethylene glycol | 10% w/v |
| Monoethanolamine | q.s. pH 8.6 to 8.8 |
| Water for injections | to 100% w/v |

TABLE 2

| INGREDIENTS | EXAMPLE | | | |
|---|---|---|---|---|
| | 11 | 12 | 13 | 14 |
| Oxytetracycline (% w/v) | 30 | 30 | 25 | 35 |
| Magnesium Oxide (% w/v) | 2.78 | 2.78 | 2.3 | 3.21 |
| N-Methyl Pyrrolidone (% v/v) | 30.0 | 60.0 | 60.0 | 60.0 |
| Sodium Formaldehyde Sulphoxylate (% w/v) | 0.4 | 0.4 | 0.40 | 0.4 |
| Water to (% v/v) | 100 | 100 | 100 | 100 |

What is claimed is:

1. A composition containing as active principle an amount of a tetracycline compound effective for antibiotic activity, either as the free base or a salt thereof with a physiologically acceptable acid, complexed with a substantially equimolar amount of a magnesium compound, solubilised in a water miscible solvent system comprising, a) glycerol formal in an amount of from about 10 to about 50% v/v; with b) polyethylene glycol 200 in an amount of from about 1 to 15% v/v;

said composition optionally containing a pH modifier in an amount sufficient to maintain a physiochemically acceptable pH, the balance being made up with water q.s.

2. A composition according to claim 1 comprising as a thickener polyvinyl pyrrolidone in an amount of up to about 10% w/v.

3. A composition according to claim 2 wherein the magnesium compound is magnesium oxide.

4. A composition according to claim 2 wherein the magnesium compound is a magnesium salt.

5. A composition according to claim 1 wherein the magnesium compound is magnesium oxide.

6. A composition according to claim 1 wherein the magnesium compound is a magnesium salt.

7. A composition according to claim 6 wherein the magnesium salt is magnesium chloride.

8. A composition according to claim 1 wherein the tetracycline compound is oxytetracycline base or its hydrochloride in an amount of from about 15 to about 35% w/v.

9. A composition according to claim 1 wherein the composition contains about 30% w/v oxytetracycline, about 40% glycerol formal, about 10% v/v poly-ethylene glycol 200 with a magnesium-containing complexing agent or stabiliser, antioxidant and water making up the balance.

10. A composition according to claim 9 wherein magnesium oxide is present in an amount of about 2.7% w/v and, as antioxidant, sodium formaldehyde sulphoxylate in an amount of about 0.4% w/v may be used.

11. A composition containing as active principle a tetracycline compound in an amount of from about 15 to about 35% w/v, either as the free base or a salt thereof with a physiologically acceptable acid, complexed with a substantially equimolar amount of a magnesium compound, solubilised in a water miscible solvent system comprising, a) glycerol formal in an amount of from about 10 to about 50% v/v; with b) polyethylene glycol 200 in an amount of from about 1 to 15% v/v;

said composition optionally containing a pH modifier in an amount sufficient to maintain a physiochemically acceptable pH, the balance being made up with water q.s.

12. A composition according to claim 11 comprising as a thickener polyvinyl pyrrolidone in an amount of up to about 10% w/v.

13. A composition according to claim 11 wherein the magnesium compound is magnesium oxide.

14. A composition according to claim 11 wherein the magnesium compound is a magnesium salt.

15. A composition according to claim 14 wherein the magnesium salt is magnesium chloride.

16. A composition according to claim 11 wherein the tetracycline compound is oxytetracycline base or its hydrochloride.

17. A composition according to claim 11 wherein the composition contains about 30% w/v oxytetracycline, about 40% glycerol formal, about 10% v/v polyethylene glycol 200 with a magnesium-containing complexing agent or stabilizer, antioxidant and water making up the balance.

18. A composition according to claim 17 wherein magnesium oxide is present in an amount of about 2.7% w/v and, as antioxidant, sodium formaldehyde sulphoxylate in an amount of about 0.4% w/v may be used.

19. An injectable composition for treatment of animals which consists of:

| | |
|---|---|
| Oxytetracycline | 300 mg |
| Magnesium oxide | 27 mg |
| Sodium formaldehyde sulphoxylate | 4 mg |
| Glycerol formal | 0.4 ml |
| Polyethylene glycol 200 | 0.1 ml |
| Monoethanolamine | q.s. pH 8.6 to 8.8 |
| Water for injections | to 1 ml | the said composition providing for administration of from about 10 to about 40 mg of oxytetracycline per kilogram of bodyweight.

* * * * *